US007242597B2

(12) United States Patent
Shodo

(10) Patent No.: US 7,242,597 B2
(45) Date of Patent: Jul. 10, 2007

(54) RECTIFIER CIRCUIT AND VISION REGENERATION ASSISTING APPARATUS HAVING THE SAME

(75) Inventor: Kenzo Shodo, Kyoto (JP)

(73) Assignee: Nidek Co., Ltd., Aichi (JP)

( * ) Notice: Subject to any disclaimer, the term of this patent is extended or adjusted under 35 U.S.C. 154(b) by 174 days.

(21) Appl. No.: 11/192,429

(22) Filed: Jul. 29, 2005

(65) Prior Publication Data

US 2006/0064141 A1     Mar. 23, 2006

(30) Foreign Application Priority Data

Aug. 4, 2004   (JP) .......................... P2004-227491

(51) Int. Cl.
*H02M 7/06* (2006.01)
*H02M 7/219* (2006.01)
(52) U.S. Cl. ..................... 363/127; 602/2; 323/911
(58) Field of Classification Search .............. 363/89, 363/125, 127; 323/911; 602/2, 54
See application file for complete search history.

(56) References Cited

U.S. PATENT DOCUMENTS

| 5,991,182 A * | 11/1999 | Novac et al. ............... 363/126 |
| 5,999,849 A | 12/1999 | Gord et al. |
| 6,421,262 B1 * | 7/2002 | Saxelby et al. ............. 363/127 |
| 2004/0054407 A1 | 3/2004 | Tashiro et al. |
| 2004/0098067 A1 | 5/2004 | Ohta et al. |
| 2004/0102843 A1 | 5/2004 | Yagi |
| 2004/0116980 A1 | 6/2004 | Ohta et al. |

FOREIGN PATENT DOCUMENTS

| JP | 08-186229 A | 7/1996 |
| JP | 2001-517056 A | 10/2001 |
| JP | 2004-89399 A | 3/2004 |
| WO | WO 02/064072 A1 | 8/2002 |
| WO | WO 02/067829 A1 | 9/2002 |
| WO | WO 02/080828 A1 | 10/2002 |

* cited by examiner

*Primary Examiner*—Jessica Han
(74) *Attorney, Agent, or Firm*—Sughrue Mion, PLLC

(57) ABSTRACT

A rectifier circuit for converting an AC voltage to a DC voltage has a first MOS transistor having a source connected to a first input terminal of an AC power supply, and also having a drain connected to an output terminal thereof, a first parasitic diode formed between the first input terminal and the output terminal, a first detection circuit, connected to the first input terminal and to the output terminal, for detecting a difference in voltage between the first input terminal and to the output terminal, a second MOS transistor, adapted to be reverse in polarity to the first MOS transistor, having a source connected to a second input terminal of the AC power supply and also having a drain connected to a ground terminal, a second parasitic diode formed between the input terminal and the ground terminal, a second detection circuit, connected to the second input terminal and the ground terminal, for detecting a difference in voltage between the second input terminal and the ground terminal, and a capacitor connected to the output terminal and the ground terminal. The first detection circuit turns on/off the first MOS transistor according to the difference in voltage, which is detected by the first detection circuit. The second detection circuit turns on/off the second MOS transistor according to the difference in voltage, which is detected by the second detection circuit.

5 Claims, 6 Drawing Sheets

RECTIFIER CIRCUIT AND VISION REGENERATION ASSISTING APPARATUS HAVING THE SAME

BACKGROUND OF THE INVENTION

The present invention is related to a rectifier circuit for converting AC voltage into DC voltage, and to a vision regeneration assisting apparatus having the rectifier circuit.

A vision regeneration assisting apparatus for vicariously executing a part of lost visual function by causing an electrode provided in an eye to output an electrical stimulation pulse signal to cells constituting a retina to stimulate it has been proposed. An apparatus (hereunder referred to as an extracorporeal image pickup type apparatus) adapted to convert outside information, which represents an image taken outside a body (that is, outside the eye), into an optical signal or an electrical signal and then transmits the signal to a device installed in the body (that is, in the eye), an apparatus (here under referred to as an intracorporeal image pickup type apparatus) adapted to form an image of outside information on a photoelectric element of a device installed in a body (that is, in the eye), and the like have been proposed as the vision regeneration assisting apparatuses.

In the apparatuses, electric power for driving the device installed in the body and that for outputting an electrical stimulation pulse signal from the electrode should be supplied from outside the body, and it is preferable for the apparatuses to perform such supply of the electric power in a noncontact manner so as to suppress infectious diseases and burdens on a patient. Thus, a method of placing a primary coil outside the body and placing a secondary coil in the body, and supplying the electrical power from outside the body into the body by electromagnetic induction has been proposed. The electrical power supplied from outside the body into the body is AC power whereas the device provided in the body is DC-driven. Thus, a rectifier circuit for converting AC voltage to DC voltage is necessary. It is desirable to miniaturize the device provided in the body more. Further, it is desirable to perform rectification more efficiently.

SUMMARY OF THE INVENTION

In view of the problem of the conventional arts, technical object to be solved by the invention are to provide a rectifier circuit, which can be miniaturized and can efficiently perform rectification, and to provide a vision regeneration assisting apparatus having the rectifier circuit.

To achieve the foregoing technical problems, according to the invention, there are provided the following circuit and apparatus.

(1) A rectifier circuit for converting AC voltage to DC voltage, comprising:

a first MOS transistor having a source connected to a first input terminal of an AC power supply and a drain connected to an output terminal;

a first parasitic diode formed between the first input terminal and the output terminal;

a first detection circuit, connected to the first input terminal and to the output terminal, for detecting a difference in voltage between the first input terminal and the output terminal;

a second MOS transistor having a source connected to a second input terminal of the AC power supply and a drain connected to a ground terminal, the second MOS transistor having polarity opposite to the first MOS transistor;

a second parasitic diode formed between the input terminal and the ground terminal;

a second detection circuit, connected to the second input terminal and the ground terminal, for detecting a difference in voltage between the second input terminal and the ground terminal; and a capacitor connected to the output terminal and the ground terminal, wherein the first detection circuit turns on/off the first MOS transistor according to the difference in voltage detected by the first detection circuit, and wherein the second detection circuit turns on/off the second MOS transistor according to the difference in voltage detected by the second detection circuit.

(2) The rectifier circuit according to (1), wherein the first detection circuit and the second detection circuit include MOS transistors, respectively.

(3) The rectifier circuit according to (2), wherein the first MOS transistor and the MOS transistor of the first detection circuit include P-MOS transistors, and the second MOS transistor and the MOS transistor of the second detection circuit include N-MOS transistors.

(4) The rectifier circuit according to (3), wherein all components thereof are formed in a monolithic structure.

(5) A vision regeneration assisting apparatus having the rectifier circuit according to (1), comprising:

an electric power acquisition unit which obtains necessary electric power by electromagnetic induction; and an electrical stimulation unit which has a plurality of electrodes and outputs an electrical stimulation pulse signal to cells constituting a retina of a patient's eye by using the DC voltage converted by the rectifier circuit from an AC voltage obtained by the electric power acquisition unit.

DETAILED DESCRIPTION OF THE PREFERRED EMBODIMENTS

Figure 1:
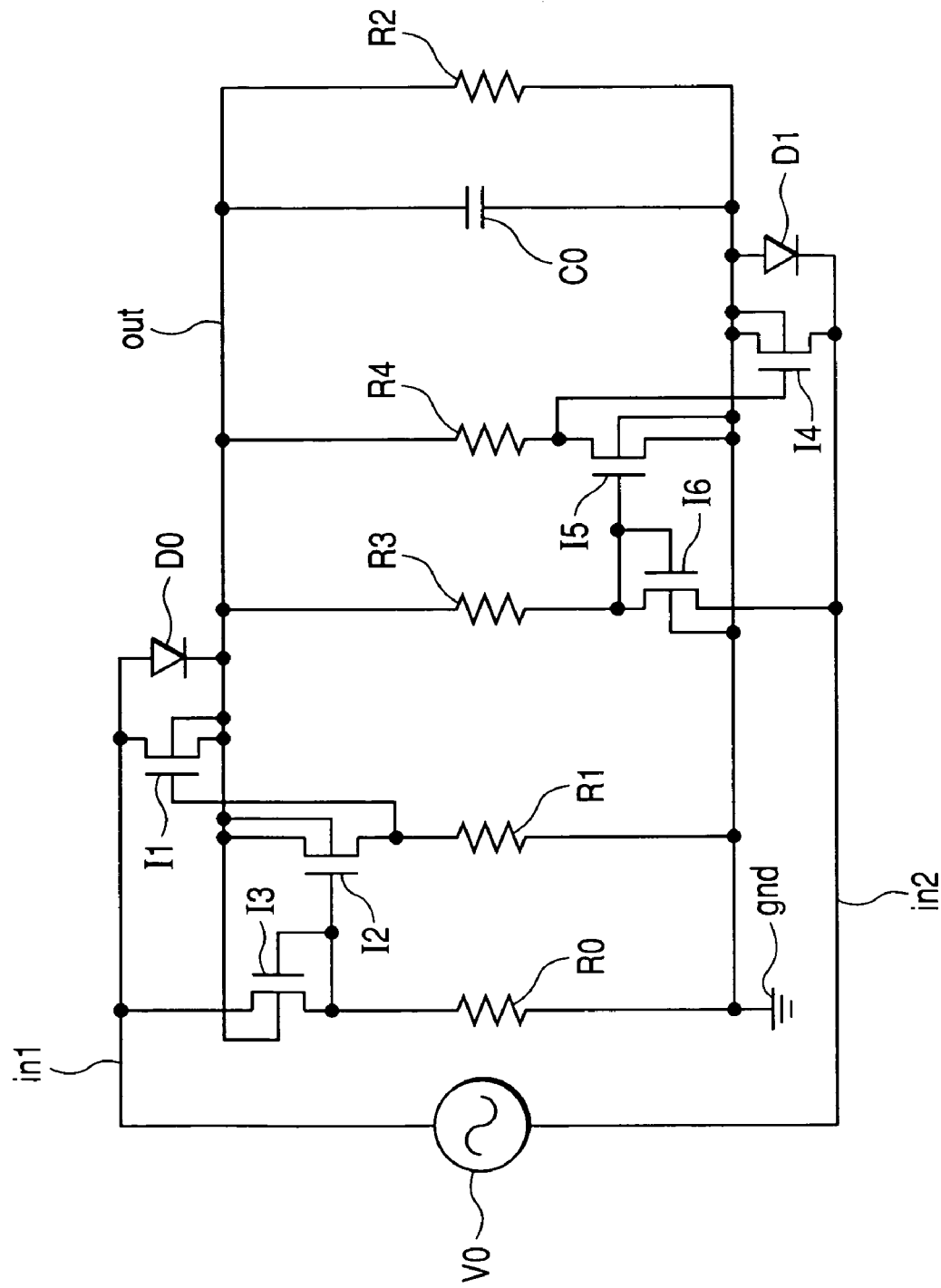
FIG. 1 is a circuit diagram showing a positive half-wave rectifier circuit in a rectifier circuit according to an embodiment of the invention.

An embodiment according to this invention will be described with reference to the accompanying drawings. FIG. 1 is a circuit diagram showing a part of a rectifier circuit used in a vision regeneration assisting apparatus according to this embodiment, which is a positive half-wave rectifier circuit.

A source of a p-channel MOS transistor I1 is connected to one input terminal in1 of an AC power supply V0. A drain of the p-channel MOS transistor I1 is connected to an output terminal out. A source of a p-channel MOS transistor I2 is connected to the output terminal out. A drain of the p-channel MOS transistor I2 is connected to a ground terminal gnd through a resistance element (or a constant current circuit)

R1, and is also connected to a gate of the MOS transistor I1. A source of a p-channel MOS transistor I3 is connected to the input terminal in1. A drain and a gate of the p-channel MOS transistor I3 are connected to the ground terminal gnd through a resistance element (or a constant current circuit) R0, and are also connected to a gate of the MOS transistor I2. A diode D0 is parasitically involved the MOS transistor I1. A anode of the diode D0 is connected to the input terminal in1, and a cathode of the diode D0 is connected to the output terminal out. A back-gate of each of the MOS transistors I1 to I3 is connected to the output terminal out.

Incidentally, the MOS transistors I2 and I3 and the resistance elements R0 and R1 serve as a detection circuit to detect a difference in voltage between the input terminal in1 and the output terminal out, and also to turn on/off the MOS transistor I1 by a gate signal.

Meanwhile, a source of an n-channel MOS transistor I4, which is reverse in polarity to the MOST transistor I1, is connected to the other input terminal in2 of the AC power supply V0. A drain of the n-channel MOS transistor I4 is connected to the ground terminal gnd. A source of an n-channel MOS transistor I5 is connected to the ground terminal gnd. A drain of the n-channel MOS transistor I5 is connected to the output terminal out through a resistance element (or a constant current circuit) R4, and is also connected to a gate of the MOS transistor I4. A source of an n-channel MOS transistor I6 is connected to the input terminal in2. A drain and a gate of the n-channel MOS transistor I6 are connected to the output terminal out through a resistance element (or a constant current circuit) R3, and are also connected to a gate of the MOS transistor I5. A diode D1 is parasitically involved the MOS transistor I4. An anode of the diode D1 is connected to the ground terminal gnd. A cathode of the diode D1 is connected to the input terminal in2. A back gate of each of the MOS transistors I4 to I6 is connected to the ground terminal gnd.

Incidentally, the MOS transistors I5 and I6 and the resistance elements R3 and R4 serve as a detection circuit to detect a difference in voltage between the input terminal in2 and the ground terminal gnd, and also to turn on/off the MOS transistor I4 by a gate signal.

Further, a smoothing capacitor C0 is connected to the output terminal out and the ground terminal gnd. Reference character R2 designates a load circuit. Incidentally, a rectifier circuit shown in FIG. 1 other than the capacitor C0 can be integrally formed in a monolithic structure.

Figure 2:
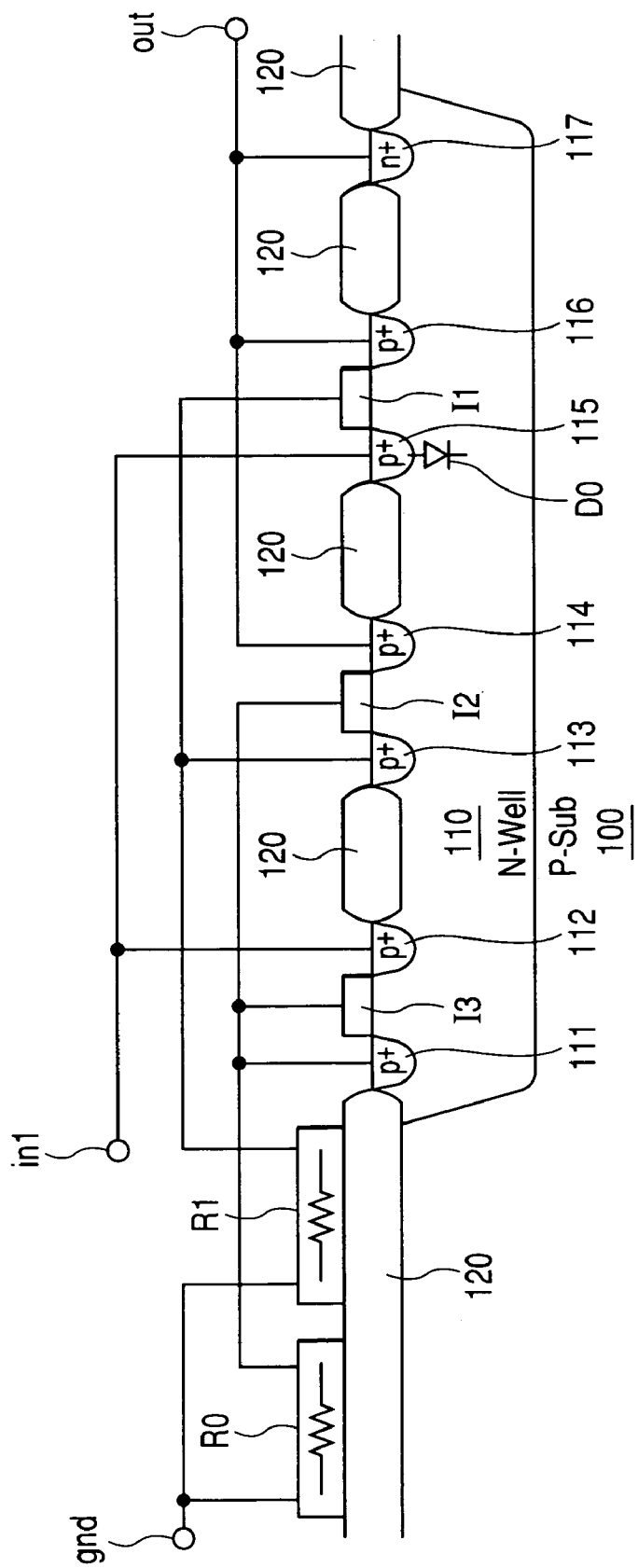
FIG. 2 is a cross-sectional diagram illustrating a positive side structure of the half-wave rectifier circuit.
Figure 3:
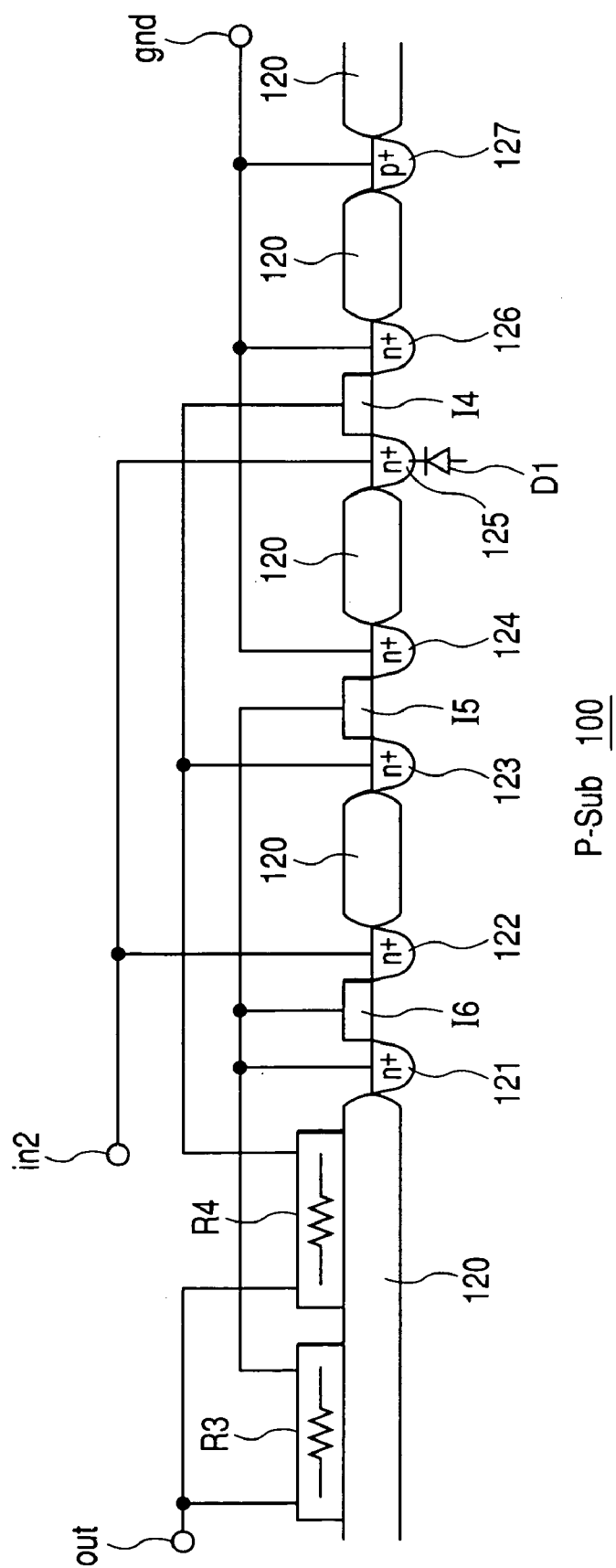
FIG. 3 is a cross-sectional diagram illustrating a negative side structure of the half-wave rectifier circuit.

FIGS. 2 and 3 are structure diagrams each illustrating a configuration in which the rectifier circuit other than the capacitor C0 shown in FIG. 1 is formed in to the monolithic structure. Incidentally, FIG. 2 is a structure diagram taken from the side of the input terminal in1. FIG. 3 is a structure diagram taken from the side of the input terminal in2.

At the side of the input terminal in1, an N-well 110 is formed on a P-substrate 100, and P$^+$ diffusion layers 111 to 116 and an N$^+$ diffusion layer 117 are formed on the N-well 110. The P$^+$ diffusion layer.111 serves as the drain of the MOS-transistor I3. The P$^+$ diffusion layer 112 serves as the source of the MOS-transistor I3. The P$^+$ diffusion layer 113 serves as the drain of the MOS-transistor I2. The P$^+$ diffusion layer 114 serves as the source of the MOS-transistor I2. The P$^+$ diffusion layer 115 serves as the source of the MOS-transistor I1. The P$^+$ diffusion layer 116 serves as the drain of the MOS-transistor I1. Incidentally, the PN-junction between the N-well 110 and the P$^+$ diffusion layer 115 constitutes the diode D0 that is parasitic on the MOS transistor I1.

Further, an insulating layer 120 made of SiO2 is formed on the P-substrate 100. The resistance elements R0 and R1 are formed on the insulating layer 120. One of the terminals of the resistance element R0 is connected to the ground terminal gnd, and the other terminal of the resistance element R0 is connected to the P$^+$ diffusion layer 111, the gate of the MOS transistor I3, and the gate of the MOS transistor I2. One of the terminals of the resistance element R1 is connected to the ground terminal gnd, and the other terminal of the resistance element R1 is connected to the P$^+$ diffusion layer 113, and the gate of the MOS transistor I1. The input terminal in1 is connected to the P$^+$ diffusion layers 112 and 115. The output terminal out is connected to the P$^+$ diffusion layers 114 and 116 and the N$^+$ diffusion layer 117.

Meanwhile, at the side of the input terminal in2, N$^+$ diffusion layers 121 to 126 and an P$^+$ diffusion layer 127 are formed on the P-substrate 100. The N$^+$ diffusion layer 121 serves as the drain of the MOS transistor I6. The N$^+$ diffusion layer 122 serves as the source of the MOS transistor I6. The N$^+$ diffusion layer 123 serves as the drain of the MOS transistor I5. The N$^+$ diffusion layer 124 serves as the source of the MOS transistor I5. The N$^+$ diffusion layer 125 serves as the source of the MOS transistor I4. The N$^+$ diffusion layer 126 serves as the drain of the MOS transistor I4. Incidentally, the PN-junction between the P-substrate 100 and the N$^+$ diffusion layer 125 constitutes the diode D1 that is parasitic on the MOS transistor I4.

Further, the insulating layer 120 made of SiO2 is formed on the P-substrate 100. The resistance elements R3 and R4 are formed on the insulating layer 120. One of the terminals of the resistance element R3 is connected to the output terminal out, and the other terminal of the resistance element R3 is connected to the N$^+$ diffusion layer 121, the gate of the MOS transistor I6, and the gate of the MOS transistor I5. One of the terminals of the resistance element R4 is connected to the output terminal out, and the other terminal of the resistance element R4 is connected to the N$^+$ diffusion layer 123, and the gate of the MOS transistor I4. The input terminal in2 is connected to the N$^+$ diffusion layers 122 and 125. The ground terminal gnd is connected to the N$^+$ diffusion layers 124 and 126 and the P$^+$ diffusion layer 127.

The rectifier circuit according to the embodiment has a structure as shown in FIGS. 2 and 3. Thus, electric power loss due to the parasitic diode can be suppressed as much as possible. The entire rectifier circuit according to the embodiment can be formed on the same substrate.

An operation of the rectifier circuit having the aforementioned configuration is described hereinafter.

When positive voltage is applied to the input terminal in1 and negative voltage is applied to the input terminal in2 so that each of the diodes D0 and D1 is forward-biased by voltage of about 0.7V, electric current flows from the input terminal in1 through the diode D0, the output terminal out, the capacitor C0, the ground terminal gnd, and the diode D1 to the input terminal in2. Thus, the capacitor C0 is charged, and the voltage at the output terminal out rises.

Since the gate of the MOS transistor I1 is connected to the ground terminal gnd through the resistance element R1, when the voltage at the input terminal in1 rises and the gate-source voltage of the MOS transistor I1 exceeds the threshold voltage of the MOS transistor, the MOS transistor I1 is turned on, so that the voltage at the output terminal out, to which the drain of the MOS transistor I1 is connected, drastically rises close to the voltage at the input terminal in1, and that the diode D0 is not forward-biased and is turned off.

Meanwhile, since the gate of the MOS transistor I4 is connected to the output terminal out through the resistance element R4, when the voltage at the input terminal in2 falls and the gate-source voltage of the MOS transistor I4 exceeds the threshold voltage of the MOS transistor, the MOS transistor I4 is turned on, the drain-source voltage of the MOS transistor I4 drastically falls, and thus the diode D1 is not forward-biased and is turned off.

Subsequently, electric current is kept supplied from the input terminal in1 to the output terminal out through the MOS transistor I1 and electric current is kept supplied from the ground terminal gnd to the input terminal in2 through the MOS transistor I4 until the voltage of the power supply V0 is maximized.

When the voltage of the power supply V0 drops, the electric current, which flows from the input terminal in1 through the MOS transistor I1, the capacitor C0, and the MOS transistor I4 to the input terminal in2, drastically decreases, the voltage at the input terminal in2 rises to be higher than that at the ground terminal gnd, and the voltage at the input terminal in1 falls to be lower than that at the output terminal out.

When the voltage at the input terminal in2 rises to be higher than that at the ground terminal gnd, the gate-drain voltage of the MOS transistor I6 biased by the charge of the capacitor C0 through the resistance element R3 rises, the MOS transistor I5 is turned on, the gate voltage of the MOS transistor I4 falls to the voltage at the ground terminal gnd, and the MOS transistor I4 is turned off.

Further, when the voltage at the input terminal in1 falls to be lower than that at the output terminal out, the gate-drain voltage of the MOS transistor I3 biased by the charge of the capacitor C0 through the resistance element R0 falls, the MOS transistor I2 is turned on, the gate voltage of the MOS transistor I1 rises to the voltage at the output terminal out, and the MOS transistor I1 is turned off.

Both the MOS transistors I1 and I4 are off, and thus electric current flowing through the load circuit R2 is supplied from the capacitor C0 during rectification is not performed, so that the voltage at the output terminal out gradually falls.

When the positive voltage and the negative voltage are applied to the input terminals in1 and in2, respectively, again, and the difference in voltage between the input terminals in1 and in2 exceeds the difference in voltage between the output terminal out and the ground terminal gnd, the MOS transistor I2 cannot maintain an on-state thereof, the gate voltage of the MOS transistor I1 drops to the voltage at the ground terminal gnd, and thus the MOS transistor I1 is turned on again. Further, the MOS transistor IS cannot maintain an on-state thereof, the gate voltage of the MOS transistor I4 falls to the voltage at the output terminal out, and thus the MOS transistor I4 is turned on again. Consequently, rectification is resumed. Electric current flows from the input terminal in1 through the MOS transistor I1, the capacitor C0, and the MOS transistor I4 to the input terminal in2, so that the capacitor C0 is charged and the voltage at the output terminal out rises.

Figure 4:
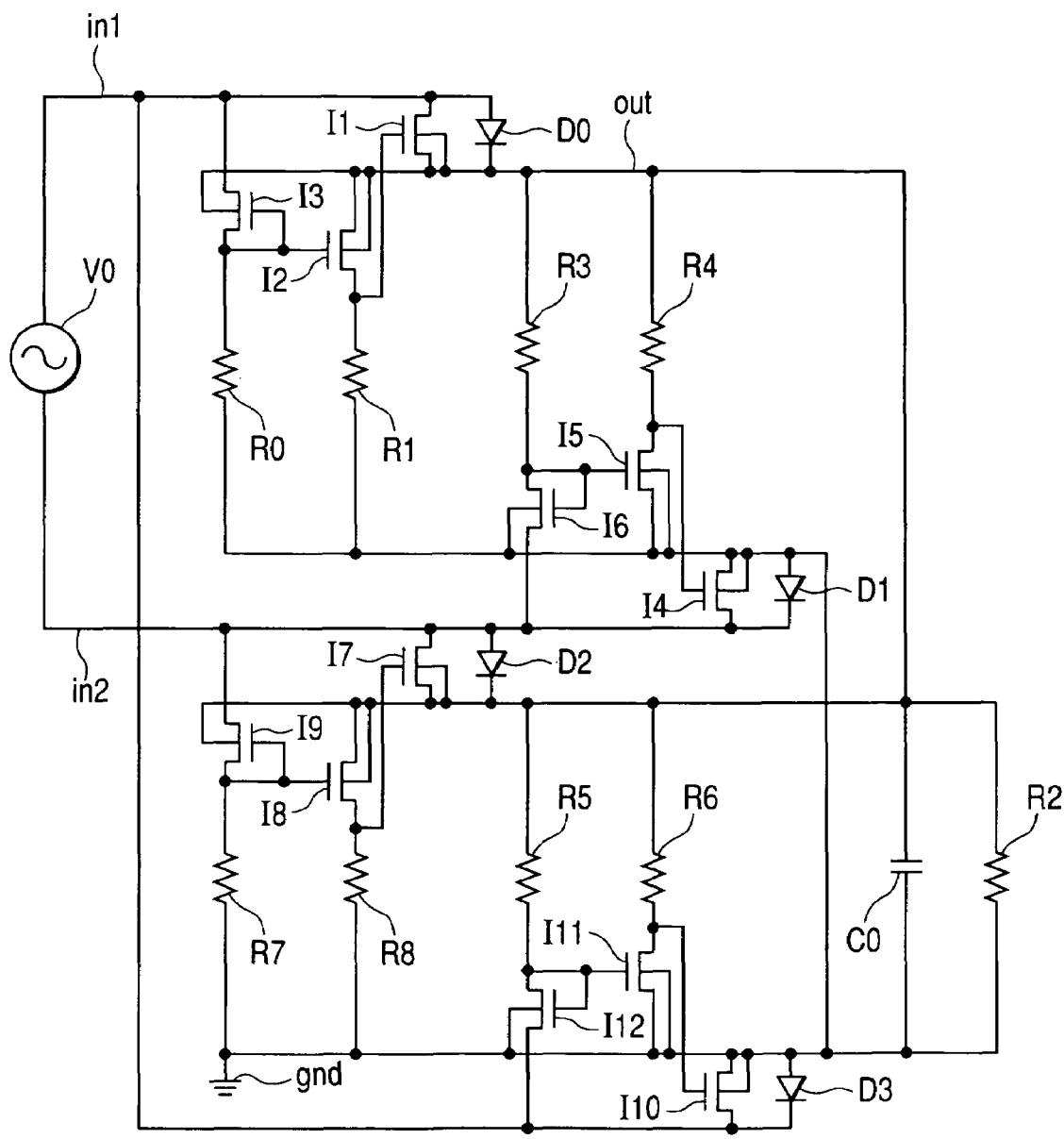
FIG. 4 is a circuit diagram showing a full-wave rectifier circuit.

Incidentally, to enhance rectifying efficiency, a full-wave rectifier circuit, which is obtained by parallel-connecting the half-wave rectifier circuits while the polarities of the input terminals in1 and in2 of the positive half-wave rectifier circuit shown in FIG. 1 are reversed, can be used. As shown in FIG. 4, a negative half-wave rectifier circuit comprising p-channel MOS transistors 17 to 19, n-channel MOS transistors I10 to I12, resistance elements R5 to R8, and parasitic diodes D2 and D3, is provided, in addition to the positive half-wave rectifier circuit shown in FIG. 1. Incidentally, in a case where negative voltage is applied to the input terminal in1 and positive voltage is applied to the input terminal in2, the MOS transistors I7 to I9 and the parasitic diode D2 serve similarly to the MOS transistors I1 to I3 and the parasitic diode D0. Further, in the case where the negative voltage is applied to the input terminal in1 and where the positive voltage is applied to the input terminal in2, the MOS transistors I10 to I12 and the parasitic diode D3 serve similarly to the MOS transistors I4 to I6 and the parasitic diode D1. The components of the full-wave rectifier circuit shown in FIG. 4 other than the capacitor C0 can be formed in a monolithic structure.

Figure 5:
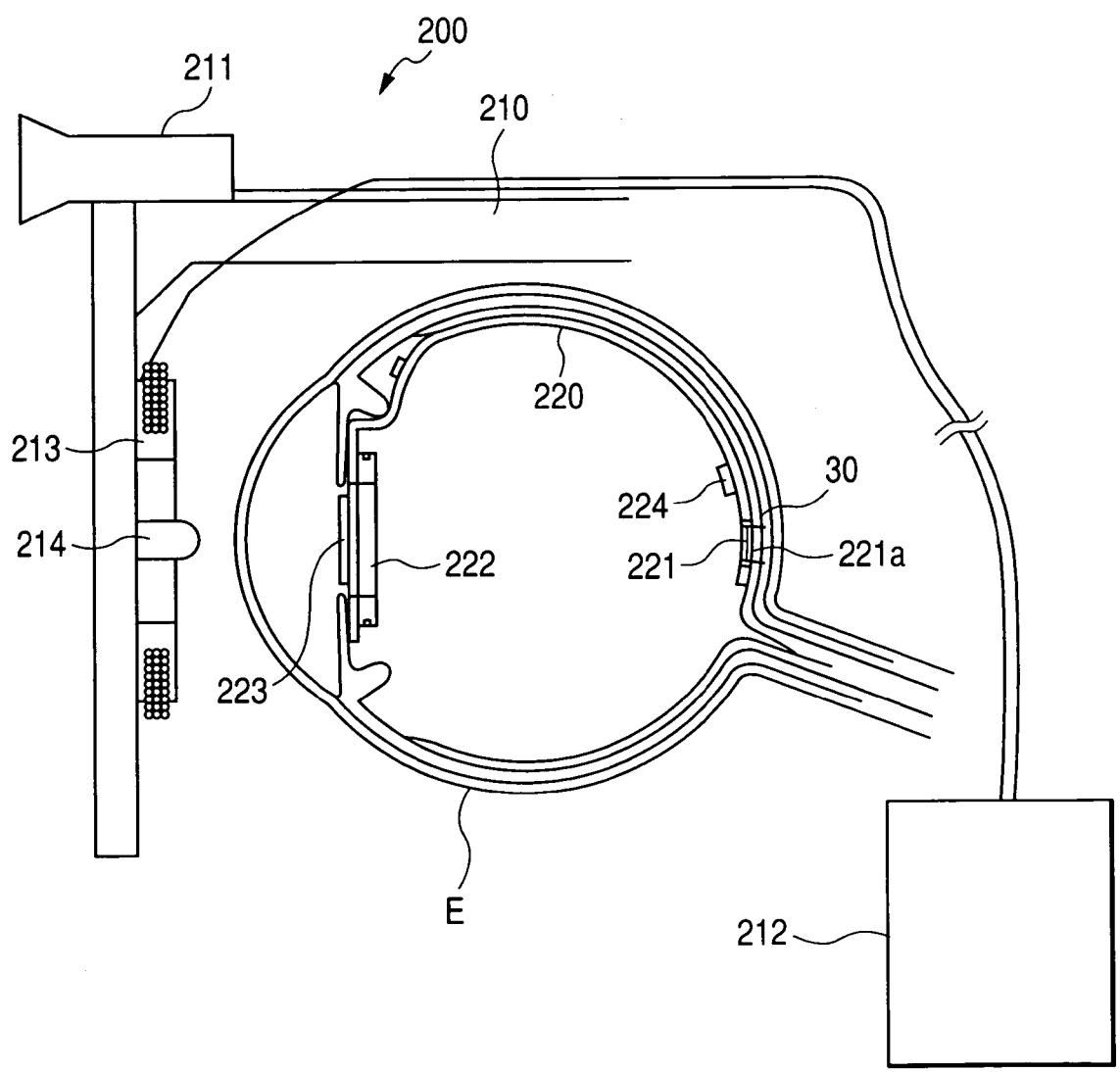
FIG. 5 is a schematic diagram illustrating a state in which a vision regeneration assisting apparatus is attached to a patient.
Figure 6:
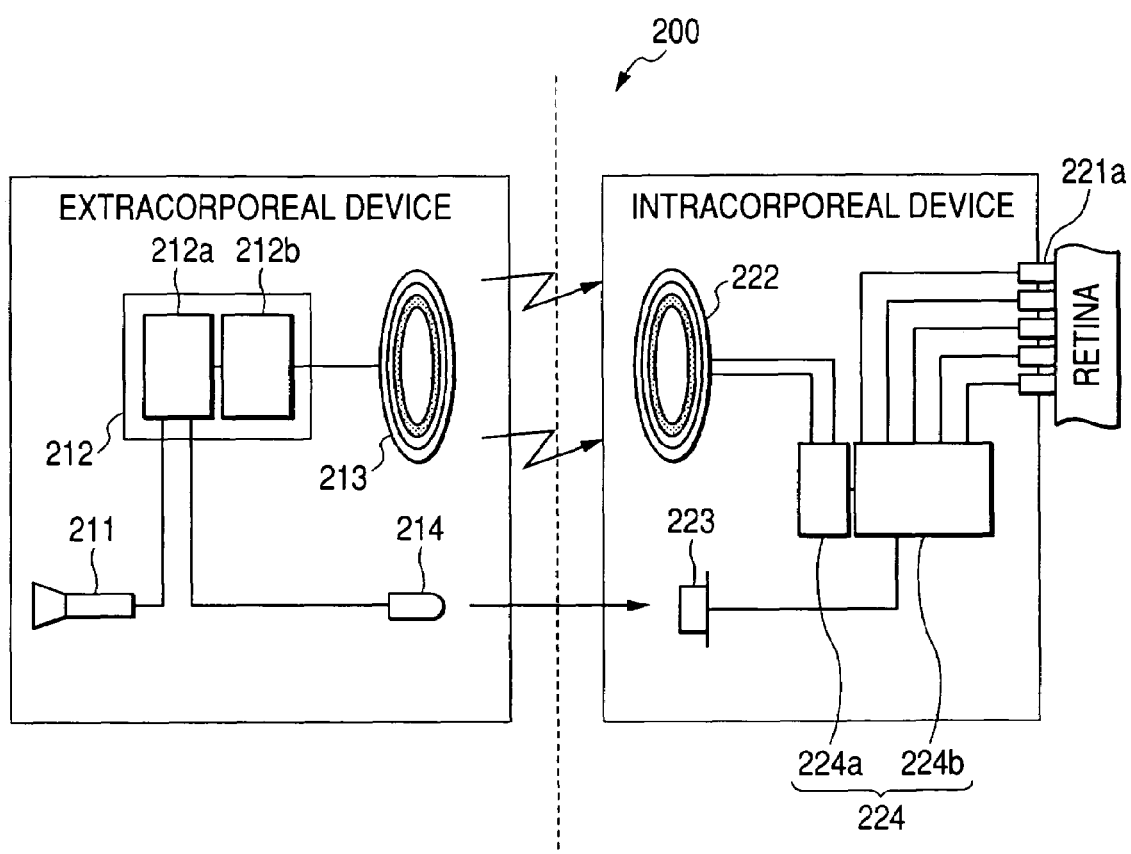
FIG. 6 is a schematic configuration diagram of the vision regeneration assisting apparatus.

Next, a vision regeneration assisting apparatus employing the rectifier circuit according to this embodiment is described hereinbelow. FIG. 5 is a schematic diagram illustrating a state in which a vision regeneration assisting apparatus is attached to a patient. FIG. 6 is a schematic configuration diagram of the vision regeneration assisting apparatus.

A extracorporeal image pickup type vision regeneration assisting apparatus 200 according to the embodiment includes an extracorporeal device for taking an image of outside, and an intracorporeal device that promotes visual restoration by giving electrical stimulation to cells constituting a retina. The extracorporeal device includes a visor 210, which is shaped like eyeglasses and is mounted on the head (or face) of a patient, an image taking unit 211 constituted by, for example, a CCD camera attached to the visor 210, an external unit 212, an electric power transmission unit 213 constituted by a primary coil and the like, and an image information transmission unit 214 for transmitting image information, obtained by the image taking unit 211, to the intracorporeal device.

The external unit 212 includes a signal conversion unit 212a, which has a computation means such as a CPU (Central Processing Unit), and a power supply unit 212b for supplying electric power to the vision regeneration assisting apparatus 200 (including the extracorporeal device and the intracorporeal device). The image taking unit 211 and the image information transmission unit 214 are electrically connected to the signal conversion unit 212a. The electric power transmission unit 213 is electrically connected to the power supply unit 212b.

In the electric power transmission unit 213, the primary coil is formed by using a magnetic body, for example, a ferrite body or a permalloy body, as a magnetic core and winding a coil wire, which is obtained by applying an insulating coating onto a copper wire or a gold wire, therearound. This electric power transmission unit 213 transmits electric power, which is supplied from the power supply unit 212b, to the intracorporeal device by electromagnetic induction so as to drive the intracorporeal device. Further, the image information transmission unit 214 is constituted by an LED, which emits infrared light, or the like, and transmits electrical stimulation pulse signal data, which is converted by the signal conversion unit 212a, to the intracorporeal device by optical communication. Incidentally, the electric power transmission unit 213 and the image information transmission unit 214 are attached to the visor 210 so as to be placed in front of a patient's eye E when the visor 210 is attached to the patient.

Meanwhile, the intracorporeal device includes a substrate 220, an electrical stimulation unit 221 including an electrode array on which many stimulation electrodes 221a for electrically stimulating cells constituting the retina, an electric power acquisition (or reception) unit 222, which is constituted by a secondary coil or the like and serves as an AC power supply, an image information reception unit 223, which receives image information from the extracorporeal device, and an internal unit 224.

The secondary coil similar to the primary coil of the electric power transmission unit 213 is formed in the electric power acquisition unit 222. The electric power acquisition unit 222 receives the electric power transmitted from the extracorporeal device (that is, the electric power transmission unit 213) by electromagnetic induction. Further, the image information reception unit 223 is constituted by a photo acceptance element or the like and receives the electrical stimulation pulse signal data from the extracorporeal device (that is, the image information transmission unit 214) by optical communication.

The internal unit 224 includes a rectifier circuit 224a for converting AC voltage obtained from the electric power acquisition unit 222 into DC voltage, and a control circuit 224b for driving the intracorporeal device by using the DC voltage converted by the rectifier circuit 224a and forming an electrical stimulation pulse signal to be outputted from the electrode 221a. The rectifier circuit 224a employs the full-wave rectifier circuit shown in FIG. 4. The electric power acquisition unit 222 corresponds to the AC power supply V0. The control circuit 224b corresponds to the load circuit R2. Further, the rectifier circuit 224a and the control circuit 224b are integrally formed in a monolithic structure and therefore the internal unit 224 can be miniaturized.

The electric power acquisition unit 222 and the image information reception unit 223 are attached to an end of the substrate 220. The electrical stimulation unit 221 and the internal unit 224 are attached to the other end of the substrate 220. Incidentally, the electric power acquisition unit 222, the image information reception unit 223, and the electrical stimulation unit 221 (the electrode 221a) are electrically connected to the internal unit 224.

An operation of the vision regeneration assisting apparatus having the aforementioned configuration will be described.

First, a lens of the patient's eye E is removed by a cataract surgery device in advance. Subsequently, an insertion opening is made by incising a part of a sclera, which part has a predetermined area and is located apart from an ear-side ring portion of the cornea of the patient's eye E at a predetermined distance (for example, about 1.5 mm), and the intracorporeal device is inserted into the eye E therefrom. At this time, as shown in FIG. 5, the substrate 220 is slid along the retina and the electrical stimulation unit 221 is disposed on the retina around a macula part. In the eye E, the electrical stimulation unit 221 is fixed by sticking a tack 30 into the retina from the substrate 220. When the tack 30 is stuck into the retina, the tack 30 penetrates through the retina, and a tip end of the tack 30 reaches a choroid or the sclera, thereby the electrical stimulation unit 221 is fixedly held on the retina. Consequently, the electrode 221a is made to always abut against the retina.

Meanwhile, as shown in FIG. 5, the image information reception unit 223 is placed at a pupil in such a manner that the image information reception unit 223 and the power acquisition unit 222 are disposed on the rear of an iris so that the image information reception unit 223 is placed at the front side thereof, and that the power acquisition unit 222 is at the back side thereof. Thereafter, the iris and the substrate 220 are stitched together. Consequently, the power acquisition unit 222 and the image information unit 223 are fixedly held.

Image information (or image data) representing an image of a target (or object), which is taken by the image taking unit 211, is converted by the signal conversion unit 212a into a signal whose frequency is within a predetermined band (electrical stimulation pulse data), and this signal is transmitted from the image information transmission unit 214 to the image information reception unit 223. The electrical stimulation pulse data received by the reception unit 223 is sent to the control circuit 224b of the internal unit 224 in the form of an electrical signal. The control circuit 224b generates an electrical stimulation pulse signal output from each stimulation electrode 221a according to the received electrical stimulation pulse data. This electrical stimulation pulse signal is output from the stimulation electrode 221a thereby to stimulate the cells constituting the retina and to promote vision restoration.

Meanwhile, the electric power supplied from the power supply unit 212b is transmitted from the electric power transmission unit 213 to the electric power acquisition unit 222. The AC voltage generated by the electric power acquisition unit 222 is efficiently converted by the rectifier circuit 224a into the DC voltage. The control circuit 224b drives the intracorporeal device by using the DC voltage converted by the rectifier circuit 224a, and forms the electrical stimulation pulse signal to be output from the stimulation electrode 221a.

Incidentally, although the image information (the electrical stimulation pulse signal data) is transmitted from the extracorporeal device to the intracorporeal device by using optical communication in this embodiment, the method of transmitting the image information according to the invention is not limited thereto. The transmission/reception of the image information can be performed by using the primary coil and the secondary coil. In this case, the apparatus may use a method of using a signal, whose frequency is within a band differing from the band within which the power signal is included, and a method of alternately transmitting the power signal and the image information signal in a time sharing manner.

Further, although the foregoing description of the embodiment has described the apparatus, in which the electrode is installed on the retina, by way of example, the apparatus according to the invention is not limited thereto. The apparatus according to the invention maybe configured so that the electrode is installed between the retina and the choroid or between the choroid and the sclera. Further, the rectifier circuit according to the invention can be applied to not only an extracorporeal image pickup type vision regeneration assisting apparatus but also an intracorporeal image pickup type vision regeneration assisting apparatus, and further can be applied to a medical device installed in the body and needs a rectifier circuit in addition to the vision regeneration assisting apparatus. Furthermore, the rectifier circuit according to the invention can be applied to an apparatus, for which a wireless IC tag is more miniaturized and for which rectification is more efficiently performed, in addition to the medical device.

What is claimed is:

1. A rectifier circuit for converting AC voltage to DC voltage, comprising:
   a first MOS transistor having a source connected to a first input terminal of an AC power supply and a drain connected to an output terminal;
   a first parasitic diode formed between the first input terminal and the output terminal;
   a first detection circuit, connected to the first input terminal and to the output terminal, for detecting a difference in voltage between the first input terminal and the output terminal;

a second MOS transistor having a source connected to a second input terminal of the AC power supply and a drain connected to a ground terminal, the second MOS transistor having polarity opposite to the first MOS transistor;

a second parasitic diode formed between the input terminal and the ground terminal;

a second detection circuit, connected to the second input terminal and the ground terminal, for detecting a difference in voltage between the second input terminal and the ground terminal; and a capacitor connected to the output terminal and the ground terminal, wherein the first detection circuit turns on/off the first MOS transistor according to the difference in voltage detected by the first detection circuit, and wherein the second detection circuit turns on/off the second MOS transistor according to the difference in voltage detected by the second detection circuit.

2. The rectifier circuit according to claim 1, wherein the first detection circuit and the second detection circuit include MOS transistors, respectively.

3. The rectifier circuit according to claim 2, wherein the first MOS transistor and the MOS transistor of the first detection circuit include P-MOS transistors, and the second MOS transistor and the MOS transistor of the second detection circuit include N-MOS transistors.

4. The rectifier circuit according to claim 3, wherein all components thereof other than the capacitor are formed in a monolithic structure.

5. A vision regeneration assisting apparatus having the rectifier circuit according to claim 1, comprising:

an electric power acquisition unit which obtains necessary electric power by electromagnetic induction; and an electrical stimulation unit which has a plurality of electrodes and outputs an electrical stimulation pulse signal to cells constituting a retina of a patient's eye by using the DC voltage converted by the rectifier circuit from an AC voltage obtained by the electric power acquisition unit.

* * * * *